United States Patent [19]

McMahon et al.

[11] Patent Number: 5,157,182
[45] Date of Patent: Oct. 20, 1992

[54] DEHYDROCYCLIZATION OF POLYSUBSTITUTED CYCLIC ORGANIC COMPOUNDS OVER COPPER ALUMINUM BORATE

[75] Inventors: Patrick E. McMahon; Larry C. Satek, both of Wheaton, Ill.

[73] Assignee: Amoco Corporation, Chicago, Ill.

[21] Appl. No.: 717,382

[22] Filed: Jun. 19, 1991

Related U.S. Application Data

[63] Continuation of Ser. No. 491,720, Mar. 12, 1990, abandoned.

[51] Int. Cl.$^5$ .................. C07C 5/333; C07D 215/06; C07D 241/42; C07D 307/79
[52] U.S. Cl. .................................... 585/411; 544/353; 546/181; 548/508; 549/32; 549/471; 585/360
[58] Field of Search ............... 585/411, 360; 544/353; 546/181; 549/32, 471; 548/508

[56] References Cited

U.S. PATENT DOCUMENTS

| | | | |
|---|---|---|---|
| 4,613,711 | 9/1986 | Pedersen et al. | 585/411 |
| 4,740,647 | 4/1988 | Hussmann et al. | 585/411 |
| 4,891,462 | 1/1990 | McMahon | 585/411 |

*Primary Examiner*—Mukund J. Shah
*Assistant Examiner*—E. Bernhardt
*Attorney, Agent, or Firm*—Frederick S. Jerome; William H. Magidson; Robert J. Wagner

[57] ABSTRACT

A dehydrocyclization process is described for producing polynuclear organic compounds by contacting a starting organic material having at least one ring moiety comprising at least two adjacent ring carbon atoms each bonded to an independently selected monovalent radical comprising at most about eight carbon atoms provided at least one of the monovalent hydrocarbon radicals comprises more than one carbon atom with a crystalline copper aluminum borate catalyst. The preferred catalyst comprises at least one member selected from the group consisting of (a) crystalline copper aluminum borate and (b) zero valent copper on a support comprising at least one member selected from the group consisting of $Al_4B_2O_9$ and the crystalline copper aluminum borate, the zero valent copper on the support being formed by the reduction of the crystalline copper aluminum borate. The process is conducted under conditions sufficient to effect cyclization between (i) a carbon atom of one of the radicals and (ii) a carbon atom of the other radical forming a dehydrocyclization product comprising a polynuclear compound wherein the new ring comprises at least 5 carbon atoms.

10 Claims, No Drawings

DEHYDROCYCLIZATION OF POLYSUBSTITUTED CYCLIC ORGANIC COMPOUNDS OVER COPPER ALUMINUM BORATE

This is a continuation of application Ser. No. 491,729, filed Mar. 12, 1990 now abandoned.

FIELD OF THE INVENTION

The present invention relates to a catalytic method for preparing polynuclear organic compounds using crystalline copper aluminum borate based catalysts. More particularly, the invention involves dehydrocyclization of a starting organic compound having at least one ring moiety comprising at least two adjacent ring carbon atoms with a first monovalent hydrocarbon radical bonded to a first ring carbon atom adjacent to a second ring carbon atom and a second monovalent hydrocarbon radical comprising at least two carbon atoms bonded to the second ring carbon atom. The process is conducted in the presence of a catalyst consisting of (a) crystalline copper aluminum borate and (b) zero valent copper on a support under conditions sufficient to effect cyclization between (i) a carbon atom of the first hydrocarbon radical and (ii) a carbon atom of the second hydrocarbon radical forming a dehydrocyclization product comprising a polynuclear compound wherein the new ring comprises at least 5 carbon atoms. For example, indene is a dehydrocyclization product formed from ortho-ethyltoluene according to the present invention.

BACKGROUND OF THE INVENTION

Indene has been used in the preparation of synthetic resins for many years, e.g., coumarone-indene or coaltar resins in which coumarone is only a small component. The commercial importance of these resins has diminished over the past decade. More recently indene has found use as a comonomer in other resins and, in high purity, as a monomer to improve the surface properties of polymers with minimal loss to vaporization due to its low vapor pressure.

Polymerization of indene and/or derivatives of indene provides valuable precursors for the formation of synthetic carbon fibers. Their use can improve carbon fiber processing and properties. As disclosed in U.S. Pat. No. 4,091,196 to Smith et al., production of a carbon fiber precursor for use in relatively sophisticated applications requires stringent control over process variables and raw materials. It will be seen that in such applications a method by which control over monomer quality may be reproducibly achieved would be advantageous.

By way of general background, McArthur, in U.S. Pat. Nos. 3,856,702, 3,856,705 and 4,024,171, discloses that it has long been the practice in the art to impregnate or otherwise distribute active catalytic metals upon support materials having desired properties of porosity, surface area, thermal and mechanical stability, and suitably inert chemical properties. In U.S. Pat. No. 4,024,171 McArthur discloses the use of catalysts comprising an aluminum borate support post treated with copper. Among the reactions disclosed for this catalyst are dehydrocyclization of $C_{6+}$ paraffins to produce corresponding aromatic hydrocarbons. However, McArthur does not disclose crystalline copper aluminum borate having the unique X-ray diffraction pattern which is characteristic of the catalyst used in the present invention.

Commonly assigned U.S. Pat. No. 4,590,324 to Satek discloses dehydrogenation of alkylaromatics containing at least two carbons in at least one alkyl group to alkenylaromatics using a catalyst comprising metallic copper on a support comprising aluminum borate. More particularly, U.S. Pat. No. 4,590,324 discloses the dehydrogenation of ethylbenzene to styrene, cumene to alphamethylstryrene and paraethyltoluene to paramethylstryene (vinyltoluene) with the catalyst. The patent does not disclose or suggest use of the catalyst for dehydrocyclization of a polysubstituted cyclic compound forming a dehydrocyclization product comprising a polynuclear compound wherein the new ring comprises at least 5 carbon atoms.

Commonly assigned U.S. Pat. No. 4,740,647 to Hussman and McMahon discloses cyclization of aliphatic moieties of 3-20 carbons using copper aluminum borate catalyst, including aliphatic moiety attached to an aromatic nucleus provided that the starting compound has an unsubstituted ring carbon ortho to the ring carbon bonded to the aliphatic moiety. In particular, 5-(orthotolyl)pentene can be dehydrocyclized to mixtures of 1,5-, 1,6-, and 2,6-dimethylnaphthalene. The patent, however, does not disclose or suggest use of the catalyst for dehydrocyclization of a polysubstituted cyclic compound to effect cyclization between (i) a carbon atom of a first hydrocarbon radical and (ii) a carbon atom of a second hydrocarbon radical wherein the hydrocarbon radicals are bonded to adjacent ring carbons on the starting cyclic compound.

Recently, U.S. Pat. No. 4,891,462 dated Jan. 2, 1990, in the name of McMahon, which is a continuation-in-part of commonly assigned U.S. Pat. No. 4,740,647 to Hussman and McMahon, discloses use of the catalyst for cyclization-dehydrogenation by contacting the catalyst with a polynuclear-fused ring aromatic compound having an ethyl group bonded to a ring carbon adjacent a bridging carbon to effect cyclization across the bridging carbon. This cyclization is between (a) the ethyl carbon furthest from the ring and (b) a second ring carbon located two carbons from the first ring carbon and separated therefrom by the bridging carbon as in the products acenaphthene and acenaphthylene from cyclization-dehydrogenation of 1-ethyl-naphthalene over copper aluminum borate. The application does not disclose or suggest use of the catalyst for dehydrocyclization of a polysubstituted cyclic compound to effect cyclization between (i) a carbon atom of a first hydrocarbon radical and (ii) a carbon atom of a second hydrocarbon radical wherein the hydrocarbon radicals are bonded to adjacent ring carbons on the starting cyclic compound.

Pedersen et al., in U.S. Pat. No. 4,613,711, discloses dehydrocyclization of certain alkylaromatics to indene or a substituted indene by contacting certain alkylaromatics in admixture with $H_2S$ with a sulfided metal oxide catalyst selected from CoO, NiO, $MoO_3$ and $WO_3$ on 60-98 weight percent of an alumina support and having a surface area (BET method) less than 100 $m^2/g$. The patent does not disclose or suggest use of any catalyst comprising either copper or boron.

Accordingly, there is a need for an improved process for production of polynuclear organic compounds by synthesis from polysubstituted organic compounds. Before the present invention, methods for obtaining many polynuclear compounds included separation of a desired compound from coal tar, petrochemical, refinery mixtures and additional purification, e.g., previous methods for obtaining high-purity indene including centrifugation, distillation and crystallization or adsorptive separation of indene-rich naphtha-cracker pyrolysis oil.

It is therefore a general object of the present invention to provide an improved method for preparing polynuclear organic compounds from certain polysubstituted ring compounds and, in particular, to provide an economical and reproducible cyclization-dehydrogenation process for preparing fused ring organic compounds wherein the new ring is formed by cyclization between groups in an ortho position to each other on a starting ring compound.

An additional need exists for a convenient method of preparing polynuclear organic compounds by synthesis from polysubstituted organic compounds without unnecessary losses to cracking and other compounds which are not intermediates in the formation of the desired polynuclear compounds, e.g., cracking products, isomerization products, and tars.

It is a further object of the invention to provide an improved method for preparing indene and/or derivatives of indene from ortho-ethyltoluene and/or substituted ortho-ethyltoluene. Other objects appear hereinafter.

In the discussion that follows, reference is made to Temperature Programmed Reduction. As discussed in Zletz copending U.S. Pat. No. 4,729,979 and Satek U.S. Pat. No. 4,590,324 (hereby incorporated by reference), this test was carried out by placing $1.5 \times 10^{-4}$ moles of copper aluminum borate in a 0.6 mm outside diameter vycor tube heated by an electric furnace. The tube was purged with helium or argon by heating to 300° C. After cooling to ambient temperature, the gas feed to the vycor tube was switched to either 5% carbon monoxide in helium or 5% hydrogen in argon and the temperature was ramped to about 850° C. at 8° C./min. The temperature was controlled and ramped by a programmer equipped with a temperature controller. The change in gas composition of the effluent was detected with a thermal conductivity cell equipped with output to a strip-chart recorder. The carbon dioxide formed was removed from the effluent by a bed of Ascarite, and the water formed was removed by magnesium perchlorate. Unless otherwise stated, pore volume, surface area and average pore radius was determined by BET nitrogen adsorption (desorption test).

SUMMARY OF THE INVENTION

The objects of this invention are provided in a dehydrocyclization process for producing polynuclear products which comprises contacting a starting organic compound having at least one ring moiety comprising at least two adjacent ring carbon atoms each bonded to an independently selected monovalent hydrocarbon radical comprising from about one to about eight carbon atoms provided at least one of the monovalent hydrocarbon radicals comprises more than one carbon atom with a crystalline-copper-aluminum-borate-based catalyst. Catalysts useful in the dehydrocyclization process of this invention comprises at least one member selected from the group consisting of (a) crystalline copper aluminum borate and (b) zero valent copper on a support comprising at least one member selected from the group consisting of $Al_4B_2O_9$ and crystalline copper aluminum borate. The process is conducted under conditions sufficient to effect cyclization between (i) a carbon atom of the first hydrocarbon radical and (ii) a carbon atom of the second hydrocarbon radical forming a dehydrocyclization product comprising a polynuclear compound wherein the new ring comprises at least 5 carbon atoms.

Starting organic compounds useful in this invention include compounds in which the two adjacent ring carbon atoms comprise a fragment of an aliphatic ring of from about 5 to about 8 carbon atoms, an aromatic ring and/or a hetrocyclic compound comprising at least one member selected from the group consisting of nitrogen, oxygen, and sulfur atoms. Starting compounds may have one or more non-hydrocarbon substituents to ring carbon atoms and/or monovalent hydrocarbon radicals, e.g., halogens, etc.

In one embodiment of the present invention, the dehydrocylization process comprises contacting a crystalline-copper-aluminum-borate-based-catalyst with a feed comprising a polysubstituted cyclic compound having a portion thereof corresponding to the formula:

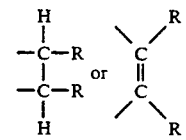

where each R is independently selected from the group consisting of alkyl having up to about 6 carbon atoms, vinyl, n-propyl, allyl, isopropyl, and phenyl groups, preferably selected from the group consisting of methyl, ethyl, vinyl, n-propyl, allyl, isopropyl, and phenyl groups, with the proviso that at least one R comprises more than one carbon atom. Catalysts useful in the dehydrocyclization process of this invention comprise at least one member selected from the group consisting of copper aluminum borate and zero valent copper on a support formed by the reduction of the crystalline copper aluminum borate. Preferred crystalline copper aluminum borate comprises $Cu_2Al_6B_4O_{17}$ having the significant X-ray diffraction lines set forth hereinbelow in Table B. The present dehydrocyclization process is conducted at conditions sufficient to effect cyclization between (i) a carbon atom of one of the radicals and (ii) a carbon atom of the other radical to obtain a dehydrocyclization product comprising a polynuclear compound where the new ring comprises at least 5 carbon atoms.

Particularly useful are feeds containing a polysubstituted cyclic compound wherein each substituent R is independently selected from the group consisting of methyl, ethyl, vinyl, n-propyl, allyl, isopropyl, and phenyl groups.

A preferred embodiment of the present dehydrocyclization process uses a starting organic material comprising ortho-ethyltoluene which is converted to products including indene, ortho-vinyltoluene, and/or mixtures thereof.

Typically the present dehydrocyclization process is carried out by contacting in a reaction zone a heterogeneous catalyst with a fluid feed, i.e., a feed in a substantially liquid and/or gaseous state. The catalyst may be used in a fixed, agitated, or fluidized bed as determined by overall process design considerations. Preferably the present dehydrocyclization process is carried out under vapor phase conditions in a reaction zone wherein the polysubstituted cyclic compound comprises from about 95 to about 1 volume percent of the gaseous composition, more preferably about 75 to about 2 volume percent.

The starting polysubstituted cyclic compound can be fed to the reaction zone neat or in admixture with other compounds including intermediate polysubstituted cyclic compounds and/or diluents. In a preferred embodiment of the present dehydrocyclization process, the gaseous feed composition comprises at least one compound selected from the group consisting of hydrogen, nitrogen, steam, alkyls of from 1 to 10 carbon atoms, benzene, toluene, and xylene.

Advantageously, an effluent from the reaction zone is transferred to a separation zone wherein the effluent is separated into at least a first fraction rich in intermediate polysubstituted cyclic compounds and a second fraction rich in a polynuclear compound which is a dehydrocyclization product. Advantageously, the first fraction is lean, i.e., not rich, in the dehydrocyclization product. Typically the separation is effected by a well-known separation processes such as fractional distillation and/or crystallization. In order to avoid excessive degradation of the effluent, a vacuum distillation can be used. In a preferred embodiment of the present dehydrocyclization process, the first fraction rich in intermediate polysubstituted cyclic compounds is further contacted under vapor phase conditions with a catalyst consisting essentially of at least one member selected from the group consisting of (a) crystalline copper aluminum borate and (b) zero valent copper on a support formed by the reduction of the crystalline copper aluminum borate. Advantageously, further contacting of the intermediate polysubstituted cyclic compounds with catalyst is done in the reaction zone by admixing the fraction rich in intermediate polysubstituted cyclic compounds with the gaseous feed.

The terms "polynuclear compound," "polynuclear organic compound" and "polynuclear-fused ring compound" can include compounds having more than two fused aromatic rings, as well as compounds having incidental ring substitution which does not prevent the cyclization-dehydrogenation reaction of the present invention from occurring. Thus, for example, while ortho-ethyltoluene can be used as the starting compound, the invention is not intended to exclude incidental substitution, for example, alkyl substitution, at the 3 through 6 positions of the ortho-ethyltoluene. Likewise, anthracenes or other higher polynuclear species are not excluded.

Dehydrocyclization of ortho-ethyltoluene produces indene and ortho-vinyltoluene as the major products of cyclization and dehydrogenation in the present process. When compared to commercially available catalysts, such as iron oxide, platinum or alumina, and platinum/rhenium on alumina, the copper aluminum borate catalyst used in the present invention results in much better conversion and selectivity to the cyclization and dehydrogenation products with a concomitant reduction in unwanted cracking reactions. Xylene, ethylbenzene, and styrene are the major by-products of such cracking. The copper aluminum borate catalyst can be post-treated with an active metal or, preferably, co-synthesized with an active metal. Preferred metals are potassium, nickel and palladium.

BRIEF DESCRIPTION OF THE INVENTION

The present invention comprises a catalytic method for preparing polynuclear organic compounds from a starting polysubstituted cyclic compound using crystalline-copper-aluminum-borate-based catalyst to effect cyclization between (i) a carbon atom of a substituent hydrocarbon radical and (ii) a carbon atom of an ortho substituent hydrocarbon radical forming a dehydrocyclization product comprising a polynuclear compound wherein the new ring comprises at least 5 carbon atoms.

Polysubstituted cyclic compounds useful in this invention include:
o-ethyltoluene
2-ethyl-1,3-dimethylbenzene
2-ethyl-1,4-dimethylbenzene
1-ethyl-2,4-dimethylbenzene
1-bromo-2-ethyl-3-methylbenzene
1-hydroxy-3-ethyl-4-methylbenzene
1-chloro-2-ethyl-3-methylbenzene
1-amino-3-ethyl-4-methylbenzene
2-ethyl-1,3,4-trimethylbenzene
2-ethyl-1,3,4,5-tetramethylbenzene
2,4-diethyl-1-methylbenzene
2-ethyl-4-vinyl-1-methylbenzene
1-propyl-2-methylbenzene
2-propyl-1,4-dimethylbenzene
1-propyl2-ethyl-4-methylbenzene
1-isobutyl-2,4-dimethylbenzene
1-(2-methylbutyl)-2-methylbenzene
1-isopropyl-2-methylbenzene (o-cymene)
2-isopropyl-1,4-dimethylbenzene
1,2-diisopropylbenzene
1-allyltoluene
1-allyl-2-ethylbenzene
1-allyl-2-ethyl-4-methylbenzene
2-(1-bromoethyl)-toluene
o-vinyltoluene
1-ethyl-2-vinylbenzene (o-ethylstyrene)
1-propyl-2-vinyl-4-methylnaphthalene
1-phenyltoluene (2-methylbiphenyl)
1-phenyl-2-ethylbenzene
2,3-diethylnaphthalene
1,2-diethylcyclohexane
2,3-diethylfuran
2,3-diethylpyrrole
2,3-diethylpyridine
2,3-diethylpyrazine
2,3-diethylthiophene
3,3'-diethyl-4,4'-dimethylbiphenyl As disclosed in Zletz, U.S. Pat. No. 4,729,979, copper aluminum borate ($Cu_{2-X}Al_{6-y}B_4O_{17}M_mM'_nM''_y$ wherein M is a divalent metal, M' is a monovalent metal, m ranges from 0 to 0.8, n ranges from 0 to 1.6, X ranges from 0 to 0.8 and is equal to the sum of $m+n/2$, M'' is a trivalent metal and y ranges from 0 to 1.2), which is at least partially reducible with hydrogen under Temperature Programmed Reduction conditions at a temperature no more than 350° C., preferably having a surface area of at least 5 $m^2$ per gram and a pore volume of at least 0.04 cc per gram, is a new catalyst and further that copper aluminum borate can be treated with a reducing agent, e.g., hydrogen, to form a catalyst comprising finely divided metallic copper (zero valent copper) on a support comprising an aluminum borate. Part of the copper in the copper aluminum borate reacts with a reducing gas at relatively low temperature (about 175° to 350° C.) to form finely divided copper on the aluminum borate support.

As disclosed in Satek, U.S. Pat. No. 4,590,324, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been substantially incorporated into copper aluminum borate crystals, and, accordingly, that X in the above formula can range from about 0.01 to 0.8, preferably about 0.05 to 0.50. Trivalent metal ions can appear as M" in the above formula, e.g., $Fe^{+++}$.

If desired, nonvolatile cations such as alkali metal (M' in the above formula) or alkaline earth metal cations can be present during the preparation of the copper aluminum borate; however, it is preferred in the present invention to introduce $K_2O$ by post-treating the calcined copper aluminum borate with $KHCO_3$ or $K_2CO_3$ solution using the incipient wetness technique.

For purposes of this invention the term "aluminum borate" is used in the generic sense to be inclusive of all aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate, comprising the X-ray diffraction pattern of $Cu_2Al_6B_4O_{17}$, such as pure or neat copper aluminum borate, copper zinc aluminum borate, aluminum borate/copper aluminum borate, copper aluminum borate/copper chromite, copper aluminum borate/alumina, copper-nickel aluminum borate, copper-palladium aluminum borate, copper-potassium aluminum borate, etc.

Briefly, the copper aluminum borate catalyst or zero valent copper on a support comprising aluminum borate for use in the cyclization-dehydrogenation process of the present invention can be prepared either from a gelled precursor in a liquid medium as disclosed in commonly assigned Zletz, U.S. Pat. No. 4,729,979, incorporated herein by reference, and in commonly assigned Satek, U.S. Ser. No. 361,278, incorporated by reference, or from a dry-mixed precursor as disclosed in commonly assigned De Simone et al., U.S. Pat. No. 4,755,497, incorporated by reference. Regardless of which technique is used, preparation of the catalyst generally involves a three-step procedure comprising: (1) combining a source of divalent copper, trivalent aluminum and boron in the form of the oxide or borate, (2) drying the composition where necessary to remove water or diluent and (3) calcining the composition at a temperature sufficiently high to form crystalline copper aluminum borate having an X-ray diffraction pattern for $Cu_2Al_6B_4O_{17}$ as set forth in Table B.

Suitable sources of copper for use in preparation of copper aluminum borate include a sol or salt of copper-(II) ions or a precursor thereof such as the acetate, formate, nitrate, carbonate, chloride, bromide, sulfate, an the like. In the liquid preparation, salts of copper(II) such as copper (II) nitrate, copper(II) acetate, and copper(II) carbonate, etc., are preferred. Copper(II) nitrate is more preferred as it behaves well in air-drying. When the source of copper(II) is a sol, oxides are preferred. Copper acetate monohydrate is preferred in the dry preparation.

The source of alumina is any material capable of producing alumina, such as aluminum nitrate, aluminum acetate, aluminum borate, etc., but preferred is a well-dispersed, liquid source such as an alumina sol.

The source of boria is a material such as borate or boric acid with pure boric acid being preferred.

Generally, these components can be combined in an aqueous or aqueous-organic liquid medium or without a liquid medium (solid-state) in approximately stoichiometric proportions sufficient to provide copper aluminum borate having the mixed metal oxide formula $2CuO \cdot 3Al_2O_3 \cdot 2B_2O_3$ or the empirical formula $Cu_2Al_6B_4O_{17}$.

The preparation of copper aluminum borate for use in the present invention can be carried out by the liquid or gel technique described in the Zletz '979 patent. Using this technique, it is generally desirable to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatilized during the subsequent drying and/or calcination step. The presence of volatile components in preparation of copper aluminum borate, such as water, $NH_3$, acetate ion, nitrate ion, etc., is advantageous in providing the copper aluminum borate with relatively high surface area and porosity desirable for most catalytic reactions. It is generally preferred to include ammonium salts or ammonium hydroxide in the above aqueous preparation to achieve the desired high surface area and porosity in the final catalyst.

Advantageously, the preparation of copper aluminum borate for use in the present invention can be carried out by the aqueous-organic liquid or gel technique described in commonly assigned Satek, U.S. Pat. No. 4,913,886 dated Apr. 3, 1990. Using this technique, it is generally desirable to form an aqueous composition comprising a volatile organic liquid having at least partial miscibility with water, a source of copper(II) ions, a source of alumina, and a source of boria at a pH in a range from about 4 to about 12; drying the composition to form a superficially dry solid; and calcining the dry solid at a sufficiently high temperature to form crystalline copper aluminum borate. Preferably, the process of producing copper aluminum borate comprises forming an aqueous composition comprising a source of copper(II) ions, a source of alumina, and a source of boria; admixing with the aqueous composition a volatile organic liquid, preferably methanol, ethanol, or N,N-dimethylformamide, containing a chemical base to form a homogeneous gel; drying the gel to form a superficially dry solid; and calcining the dry solid at a sufficiently high temperature to form crystalline copper aluminum borate.

Suitable basic compounds include oxides, hydroxides and salts of alkali metal elements, ammonium hydroxide, and hydroxides of organic cations, such as methylammonium hydroxide or tetramethylammonium hydroxide. Preferred chemical bases comprise at least one quaternary ammonium cation selected from the group consisting of tetramethylammonium, tetraethylammonium, benzyltrimethylammonium, trimethyl-n-octylammonium, dibenzyldimethylammonium, and cetyltrimethylammonium. The presence of the ammonia as well as other volatile components in the gelled mixture, such as acetate ion, nitrate ion, etc., is advantageous in providing the final calcined solid with sufficiently high surface area and porosity desirable for catalytic reactions.

Typically, the pH of the aqueous mixture is in a range from about 4 to about 12. If the reaction media is too acidic or too basic, the desired solid generally will not form or other contaminating phases will form in addition to the desired product. To some extent the pH of the reaction mixture controls surface properties of the final calcined solid material. Preferably, the pH of the reaction mixture is in a range from about 4.5 to about 10, more preferably about 5 to about 9, in order to gel the reaction mixture.

The gelled mixture is mildly dried for anywhere from a few hours to a few days at varying temperatures, typically about 20° to about 225° C., to form a dry cake which is a copper aluminum borate precursor. Advantageously, the gelled mixture is allowed to air-dry, usually for about 1 to 3 days, followed by vacuum drying, typically at a pressure of about 0.3 atmosphere for about 15 to 25 hours at about 100° C. to 150° C. with a purge of dry gas, such as nitrogen.

Among the advantages offered by a liquid or gel preparation is that it eliminates the need to grind solid reagents to uniform size and blend dry solids to obtain a homogeneous mixture in the preparation of copper aluminum borate precursor, thus greatly simplifying the overall preparation of the catalyst. The aqueous-organic method also enhances the consistency (i.e., reproducibility) of the catalyst and enables the catalyst to be improved by incorporation of active metals using a sol or solution in the aqueous-organic mixture. Because the crystalline copper aluminum borate is formed at lower temperatures during calcination, porosity and surface area can be controlled to predetermined levels, even up to surface areas of about 200 $m^2/g$ and higher. In this process for producing copper aluminum borate, a homogeneous gel is formed of an aqueous-organic medium comprising a volatile organic liquid having at least partial miscibility with water. Useful volatile organic compounds typically have normal boiling points in a temperature range downward from about 140° C. Suitable organic compounds include alcohols, ethers, aldehydes and ketones having from about 1 to about 5 carbon atoms per molecule, such as methanol, ethanol, 2-propanol, 2-butanol, 2-methyl-2-propanol, 2-propen-1-ol, methoxymethane, methoxyethane, 1-methoxypropane, 2-methoxypropane 2-ethoxypropane, 1,3-dioxane, 1,4-dioxane, propanone, butanone, 3-pentanone, 2-pentanone, and N,N-dimethylformamide. Of these organic compounds methanol, ethanol, and N,N-dimethylformamide are preferred.

Alternatively, copper aluminum borate catalyst useful in the present invention can be conveniently prepared using a solid-state method as disclosed in De Simone et al., commonly assigned U.S. Pat. No. 4,755,497, incorporated herein by reference. The solid-state preparation obviates the time-consuming and economically costly step of drying the catalyst precursor prior to calcining.

Briefly, the solid-state preparation of copper aluminum borate comprises (1) dry-mixing powdered reagents comprising suitable precursors of copper oxide (CuO), aluminum oxide ($Al_2O_3$), and boron oxide ($B_2O_3$) with at least about 3 wt. % on a dry-solids basis of a suitable solid binder to form a superficially dry copper aluminum borate precursor; (2) compacting the dry precursor; and (3) calcining the precursor at a sufficiently high temperature to form crystalline copper aluminum borate. The terms "dry," "dry-mixed," "solid state," "solid," and "superficially dry" are intended to denote conditions, processes, or reagents which are essentially free of liquid materials. These terms are not intended to exclude the presence of ambient atmospheric moisture of the water of hydration in solid reagents. The terms "precursor," "copper aluminum borate precursor," "dry-mixed precursor," etc., denote compositions which, upon calcination at a sufficiently high temperature, result in crystalline copper aluminum borate.

In the dry preparation, the solid reagents comprising suitable precursors of copper aluminum borate should be ground to a powder, individually or as a combination, through a 0.25 mm screen in a high-speed grinder. It is important that similar particle sizes of all reagents be attained in order that the solid state reaction to form crystalline copper aluminum borate proceeds as uniformly as possible upon calcination. Following grinding, a superficially dry mixture is prepared by combining the powdered dry reagents with about 3 to 20 wt. % of a suitable solid binder.

A suitable solid binder is one which is capable of holding the powdered reagents together following compaction in a pellet press or extrusion apparatus and which will burn away upon calcination, thus imparting porosity to the pellet. Preferred binders are solid stearins and the like, graphite, or mixtures thereof. Sterotex, a commercially available vegetable stearin, is particularly well-suited as it burns off at a lower temperature than graphite and results in a better catalyst. The preferred amount of binder is at least about 3% by weight of the powdered reagents on a dry solids basis, but up to about 20% may be employed. About 5 wt. percent of the binder is recommended. The binder material can be combined with the powdered reagents using a conventional mixing apparatus for a period of about 10 to about 60 minutes. After the above-prescribed mixing of the powdered reagents and solid binder is completed, the resulting superficially dry mixture can be either extruded or pelletized using conventional techniques and apparatus.

The superficially dry precursor is calcined, preferably at a temperature within the range of about 650° to about 1000° C., for a reaction time that is sufficient to effect formation of crystalline copper aluminum borate, typically a reaction time within the range of about 2 to about 30 hr. Samples of material can be removed during calcination to check the degree of crystallization and to determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removed impurities such as excess boria without destroying the crystalline material formed, and then mildly dried for anywhere from a few hours to a few days at varying temperatures, typically about 50° to about 225° C., to form a dry cake which can then be treated as required for its intended use.

The solid materials made by this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegetable stearine produced by Capital City Products, Co., Columbus, Ohio), or other binders well known in the art.

In either the liquid or solid state preparation, part of the copper salts or aluminum component can be replaced with divalent and/or trivalent metal salts as described above.

The catalyst precursor prepared by either of the methods described above should be calcined at a temperature in the range of from about 650° to about 1000°, preferably at least about 800° C., for about 1 to 24 hours, typically in air. The higher the calcination temperature, the shorter the calcination time. Calcinations below about 800° C. tend to provide a catalyst which has low activity for the reaction of the present invention. Other things being equal, the higher the calcination temperature the lower the surface area and porosity of the copper aluminum borate. Thus, at calcination temperatures exceeding 1000° C., the catalytic activity of the resultant material is substantially diminished. In the present invention, the copper aluminum borate precursor mixture is initially calcined at a temperature of about 200° to 400° C., preferably about 300° C. for 3 to 4 hours to burn off volatiles, followed by an increase in temperature to preferably between 780° and 860° C. for about 3 to 8 hours. The preferred calcining regime is 820° C. for about 4 to 8 hours.

Copper aluminum borate or copper on a support comprising aluminum borate can be treated with any of the metals or metal compounds conventionally used in catalysis. Copper aluminum borate, for example, can be treated or doped with an alkali metal or alkaline earth metal compound. Any one or more of the transition metals or compounds can be utilized such as the metals of Groups IB, IIB, IIIB, IVB, VB, VIB, VIIB and VIII of the Periodic Table. Suitable metals include zinc, cadmium, copper, silver, chromium, molybdenum, scandium, tungsten, manganese, titanium, rhenium, iron, cobalt, nickel, ruthenium, rhodium, palladium, osmium, iridium, vanadium, platinum, etc. These metals can be present in a concentration of from 0.01 to 30% by weight of the copper aluminum borate catalyst or copper on aluminum borate. These metals or metal compounds can be applied as salts, oxides, etc., and, if desired, thermally decomposed to give the corresponding metal or oxides. Catalytically active copper aluminum borate which is at least partially reducible with hydrogen under Temperature Programmed Reduction (TPR) at a temperature of no more than 350° C. and which has a surface area of at least 5 square meters per gram and a pore volume of at least 0.04 cc per gram is the subject of commonly assigned Satek, U.S. Pat. No. 4,590,324; Kouba et al., U.S. Pat. No. 4,613,707; Zletz et al., U.S. Pat. No. 4,645,753; Zletz, U.S. Pat. No. 4,729,979; De Simone et al., U.S. Pat. No. 4,755,497; and copending application of Zletz, U.S. Ser. No. 285,103, filed Dec. 15, 1988. These applications disclose the preparation, characterization and utility of copper aluminum borate and are hereby incorporated by reference.

If desired, nonvolatile cations such as alkali metal or alkaline earth metal cations can be present during the preparation of the copper aluminum borate precursor. Suitable alkali metal and alkaline earth metal compounds include the oxides, hydroxides and salts of lithium, sodium, potassium, rubidium, cesium, magnesium, calcium, strontium, and barium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium, in the form of the oxide or in a form readily convertible to the oxide, is preferred. The aluminum borate can be treated with from about 0.05 to 50 wt. % dopant based on the weight of the aluminum borate. The alkali metal or alkaline earth metal compound can be dry-blended with the aluminum borate; dissolved in a suitable solvent, preferably water; mixed with the aluminum borate and dried; or aqueous solutions of same can be added to feedstocks going to a reactor containing the aluminum borate catalyst.

Advantageously, a crystalline material formed according to this invention is formed or combined with from about 0.05 to about 50 wt. % of at least one compound of a metallo element selected from the group consisting of Groups IA, IIA, IIB, VIB an VIII of the Periodic Table based on the weight of crystalline material.

Suitable alkali metal (Group IA), alkaline earth metal (Group IIA), low melting metal (Group IIB), brittle metal (Group VIB), and heavy metal (Group VIII) compounds include the oxides, hydroxides and salts of lithium, sodium, potassium, rubidium, cesium, magnesium, calcium, strontium, barium, chromium, zinc, cadmium, lanthanum, cerium, and thorium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium and chromium, in the form of the oxide or in a form readily convertible to the oxide, are preferred. The solid materials formed according to this invention can be treated with from about 0.05 to 50 wt. % dopant based on the weight of the solid material. The metallo compound or compounds can be dry-blended with the aluminum borate; dissolved in a suitable solvent, preferably water; mixed with the solid material and dried; or aqueous solutions of same can be added to feedstocks going to a reactor containing the solid material catalyst.

Particularly useful is the fact that when these solid catalyst compositions are used in liquid and/or gas-phase processes, the products of chemical conversion are easily separated from the solid catalyst material. Also useful is the fact that when these solid catalyst compositions are used in such fluid-phase processes, the active metallo element components are only slowly extracted, leading to longer catalyst lifetime.

Preferably, where the catalyst is to be used for the dehydrogenation catalyst, density is desirably in the range of from about 0.48 g/ml to about 1.1 g/ml, and preferably in the range of about 0.5 /g/ml to about 0.8 g/ml.

After the copper aluminum borate precursor has been dried, calcination of the precursor is carried out at a temperature in the range of from about 650° to about 1000° C., preferably at least about 700° C. if the catalyst is to be used for syngas conversion (as disclosed in commonly assigned copending Zletz, U.S. Ser. No. 285,103) and at least about 800° C. if the catalyst is to be used for dehydrogenation (as disclosed in Satek, U.S. Pat. No. 4,590,324) for about 0.1 to 24 hours, typically in air. The higher the calcination temperature, the shorter the calcination time. Calcinations below about 800° C. tend to provide a catalyst that is more active in oxychlorination of methane. Calcinations above about 800° C. tend to provide a green crystalline material that is more active in dehydrogenation reactions than the green crystalline material obtained below about 800° C. Other things being equal, the higher the calcination temperature, the lower the surface area and porosity of the copper aluminum borate. In the present invention, the superficially dry copper aluminum borate precursor mixture is calcined to a temperature in a range from about 650° to about 900° C., typically for 3-24 hours, preferably to a temperature between 650° and 860° C. for about 8 to about 20 hours. The most preferred calcining temperature has been bound to be in a range of from about 680° to about 840° C.

When copper aluminum borate is used as a catalyst in the dehydrogenation of organic compounds or in a reaction medium containing a reducing gas, at least part of the copper in the copper aluminum borate is converted into finely divided copper on an aluminum borate support. In some reactions, such as in the dehydrogenation of alkylaromatics to alkenylaromatics, a significant amount of the copper in the still active catalyst can be present as finely divided copper metal on an aluminum borate support, i.e., in the aluminum borate matrix. In other cases, the active catalyst always contains some copper aluminum borate. If part of the copper in copper aluminum borate is replaced with another divalent metal, for example zinc or nickel, copper in the compound is still reducible to metallic copper at relatively low temperature.

If neat copper aluminum borate having the empirical formula $Cu_2Al_6B_4O_{17}$ is viewed as having the structure $3Al_2O_3.2CuO.2B_2O_3$, the reduction with CO or $H_2$ can be represented in its simplest terms as follows:

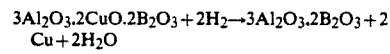

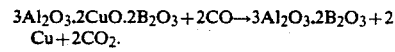

X-ray diffraction patterns of the products indicate that the aluminum borate crystal has the formula $2Al_2O_3.B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB and aluminum borate. The X-ray diffraction patterns in Table A show the significant lines for substantially fully reduced CuAB (copper on aluminum borate) of this invention, unreduced CuAB of this invention, CuAB of Uhlig, $Al_4B_2O_9$ and copper.

X-ray data were determined by standard techniques. The radiation was the K-alpha doublet of copper, and a proportional counter spectrometer with a strip chart pen recorder was used. The peak heights, I, and the positions as a function of 2 times theta, where theta is the Bragg angle, were read from the spectrometer chart. From these the relative intensities, 100 I/I$_0$, where I$_0$ is the intensity of the strongest line or peak, and d (obs.), the interplanar spacing in Angstroms, corresponding to the recorded lines, were calculated. In Table A, the relative intensities are given in terms of the symbols VVS=very very strong (>100), VS=very strong (80-100), S=strong (50-80), M=Medium (20-50), W=weak (10-20) and VW=very weak (<10).

TABLE A

| (d) Angstroms | Cu on AB | CuAB | Uhlig CuAB | $Al_4B_2O_9$ | Cu |
|---|---|---|---|---|---|
| 7.50 ± .1 | | VW-M | M | | |
| 5.29 ± .05 | VS | VS | VS | VS | |
| 5.00 ± .05 | | S | S | | |
| 4.92 ± .03 | W-M | | | W | |
| 3.73 ± .03 | | W-M | W | | |
| 3.64 ± .03 | | VW-W | VW | | |
| 3.58 ± .03 | VW-M | | | VW | |
| 3.35 ± .03 | VW-M | W | W | M | |
| 2.98 ± .03 | | VW-W | W | | |
| 2.84 ± .03 | | VW-W | VW | | |
| 2.78 ± .02 | VW | | | | |
| 2.64 ± .02 | M | M-S | M | M | |
| 2.61 ± .02 | | W-M | W | | |
| 2.50 ± .02 | | W-M | VW | | |
| 2.45 ± .02 | W-M | | | W | |
| 2.26 ± .02 | | W-M | W | | |
| 2.22 ± .02 | W | | | VW | |
| 2.16 ± .02 | | M | W | | |
| 2.13 ± .02 | M | | | W-M | |
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction lines of the $Al_4B_2O_9$ and copper.

The significant X-ray diffraction lines for copper aluminum borate are set forth below in Table B.

TABLE B

| (d) Angstroms | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

Condition sufficient to effect cyclization in the catalytic process of the present invention comprises a temperature in a range of from about 400° to about 700° C., preferably about 450° to about 650° C., more preferably about 500° to about 630° C. and a pressure in a range of from about 0.1 to about 50 atmospheres, preferably about 0.25 to about 10 atmospheres, more preferably about 0.5 to about 2 atmospheres. When the catalytic process is conducted in a continuous mode, useful weight hourly space velocities (WHSV) are generally in a range of from about 0.01 to about 5.0 hr$^{-1}$, preferably about 0.02 to about 2.0 hr$^{-1}$, more preferably about 0.04 to about 1 hr$^{-1}$.

Dehydrocyclization products of the present invention include the following polynuclear compounds wherein the new ring comprises at least 5 carbon atoms:

indene
4-methylindene
5-methylindene
6-methylindene
4-bromoindene
5-hydroxyindene
4-chloroindene
5-aminoindene
4,5-dimethylindene
4,5,6-trimethylindene
5-ethylindene
5-vinylindene
2-methylindene
2,5-dimethylindene
2-methylnaphthalene
2,6-dimethylnaphthalene
2,3-dimethylnaphthalene
3-methylindene
3,5-dimethylindene
1,4-dimethylnaphthalene
3-bromoindene
indene
naphthalene
fluorene
phenanthrene
anthracene
tetralin
decalin
benzofuran
indole
quinoline
quinoxaline
benzothiophene
5-(5'-indenyl)-indene

EXAMPLES

General

In the following examples demonstrating cyclization-dehydrogenation according to the present invention, the reactions were carried out in a gas-phase, flow-through, fixed-bed reactor. Reactors were ⅜ inch O.D. by 21 inch quartz tubes fitted with a ¼ inch thermowell; catalyst frit was located approximately 2 inches below center. This allowed catalyst to be loaded in such a way as to minimize empty reactor space in the hottest reactor zones. Heat was provided by single-zone, Lindberg furnaces regulated by standard on-site controllers. Liquid reactants were fed and regulated by Harvard syringe pumps. Gaseous reactants were regulated with micrometering valves and measured by gas bubble meters. Liquid products were collected in a series of traps employing water/ice and a watercooled spiral condenser. Gaseous products were not collected.

Reactants and products were identified and quantified by GC analysis. Product identities were determined and confirmed by GC of authentic samples and GC/mass spectroscopy analysis.

Product concentrations reported have been calculated from area percent data.

EXAMPLE 1

Copper nitrate hydrate (233.0 g, 1.00 mol) in 200 mL deionized water, alumina sol (1653.2 g of a 9.26% Al$_2$O$_3$, 1.50 mol) and boric acid (123.9 g, 2.00 mol) dissolved in 600 mL of warm deionized water were added to a 1 gal Waring blender with mixing. A total of 800 mL of 20% tetramethylammonium hydroxide was added to the mixture, in portions with mixing, to obtain a gel having a final pH of 5.7. The gel was spread onto trays for drying and vacuum dried at 120° C. in a nitrogen purge at 0.3 atm overnight. A portion, 150 g, was placed in a calcining oven and calcined by the following program:

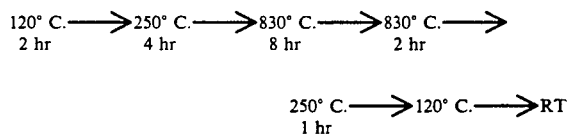

The material, 78.2 g, was removed from the oven and identified as Example 4. ICP analysis showed 22.6% copper, 27.4% aluminum, 7.3% boron. The material exhibited an x-ray powder diffraction pattern comprising significant lines substantially as described in Table B for copper aluminum borate.

EXAMPLE 2

Using the general reaction procedures summarized above, copper aluminum borate of Example 1 was loaded into a quartz reactor tube. The starting material, o-ethyltoluene, was fed to the reactor at WHSV of 0.05. The diluents used were toluene and nitrogen at a diluent ratio of 40:1. The reaction was carried out at 600° C. After 30 hr on stream, conversion was 77% and selectivity to the products o-vinyltoluenene, Indene, and Indan was 88%. Xylenes and other products of cracking made up the balance of 12%. Product distribution of these products normalized to 100% was as follows:

| | |
|---|---|
| Indene | 58% |
| o-vinyltoluenene | 27% |
| Xylenes/other | 12% |
| Indan | 3% |

EXAMPLE 3

Using the general reaction procedures summarized above and copper aluminum borate of Example 1, this example illustrates performance of the catalyst under several varied conditions. The starting material, o-ethyltoluene, was fed to the reactor at WHSV of from 0.05 to 0.4. The diluents used were toluene and nitrogen at a diluent ratio of from 6:1 to 40:1. Times on o-ethyltoluene ranged up to 189 hr. The conditions and results of these runs in which the reaction was carried out at 600° C. are reported in the following Table I.

TABLE I ortho-Ethyltoluene to Indene[1]

| Dilution Ratio | WHSV hr$^{-1}$ | Conversion mole % | Selectivity[2] | | |
|---|---|---|---|---|---|
| | | | o-Vinyltoluene mole % | Indan mole % | Indene mole % |
| 13/1 | 0.10 | 35 | 57 | 4 | 28 |
| 8/1 | 0.10 | 66 | 41 | 3 | 49 |
| 10/1 | 0.15 | 37 | 53 | 6 | 30 |
| 7/1 | 0.30 | 21 | 74 | 2 | 15 |
| 6/1 | 0.40 | 16 | 80 | 1 | 10 |

[1]Temperature at 600° C.
[2]Balance of liquid product is xylene and other cracking products

EXAMPLE 4

Copper nitrate hydrate (232.9 g, 1.00 mol) dissolved in 200 mL warm deionized water, alumina sol (1728.0 g of a 8.88% Al$_2$O$_3$ sol, 1.50 mol), and boric acid (124.0 g, 2.00 mol) dissolved in 600 mL warm deionized water were placed into a 1 gal Waring blender and mixed for about 2 min. The pH of the mixture was 3.2. A total of 800 mL of 2 0% tetramethylammonium hydroxide in methanol solution was added to the mixture, in several portions, with mixing to obtain a gel which had a final pH of 5.9. The gel was first air dried on tray and then vacuum dried at 120° C. in a nitrogen purge at 0.3 atm overnight. The dry material was calcined according to the following program:

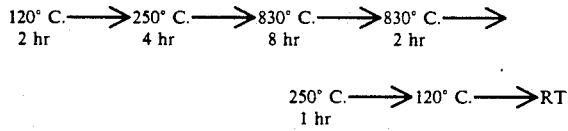

The resulting material had a BET surface area of 37 m$^2$/g, an ICP analysis of 20.0% copper 25.7% aluminum, 7.1% boron. This material, identified as Example 4, exhibited an X-ray powder diffraction pattern comprising significant lines substantially as described in Table B for copper aluminum borate.

EXAMPLE 5

Using the general reaction procedures summarized above, copper aluminum borate of Example 4 was loaded into a quartz reactor tube. The starting material, o-ethyltoluene, was fed to the reactor at WHSV of 0.05. The diluents used were toluene and nitrogen at a diluent ratio of 40:1. The reaction was carried out at 600° C. After 112 hr on stream conversion was 51% and selectivity to the products o-vinyltoluenene, Indene, and Indan was 93%. Xylenes and other cracking products account for a balance of 7%. Product distribution of these products normalized to 100% was as follows:

| | |
|---|---|
| Indene | 40% |
| o-vinyltoluenene | 51% |
| Xylenes/other | 7% |
| Indan | 2% |

EXAMPLE 6

Using the general reaction procedures summarized above and copper aluminum borate of Example 4, this example illustrates performance of the catalyst under several varied conditions. The starting material, o-ethyltoluene, was fed to the reactor at WHSV of from 0.02 to 0.35. The diluents used were toluene and nitrogen at a diluent ratio of from 4:1 to 40:1. Times on o-ethyltoluene ranged up to 200 hr. The conditions and results of these runs in which the reaction was carried out at 600° C. are reported in the following Table II.

TABLE II ortho-Ethyltoluene to Indene[1]

| Dilution Ratio | WHSV hr$^{-1}$ | Conversion mole % | Selectivity[2] | | |
|---|---|---|---|---|---|
| | | | o-Vinyltoluene mole % | Indan mole % | Indene mole % |
| 38/1 | 0.02 | 62 | 45 | 2 | 45 |
| 40/1 | 0.05 | 51 | 53 | 3 | 37 |
| 15/1 | 0.08 | 36 | 58 | 3 | 29 |
| 10/1 | 0.15 | 28 | 62 | 4 | 22 |
| 4/1 | 0.35 | 22 | 70 | 3 | 16 |

[1]Temperature at 600° C.
[2]Balance of liquid product is are xylene and other cracking products

COMPARATIVE EXAMPLE A

This example illustrates dehydrocyclization of propylbenzene using the general reaction procedures summarized above and copper aluminum borate of Example 4. The starting material, propylbenzene, was fed to the reactor at WHSV of 0.02. The diluents used were benzene and nitrogen at a diluent ratio of 40:1. The reaction was carried out at 600° C. Conversion was 91%. Product distribution was as follows:

| | |
|---|---|
| Indene | 23% |
| Ethylbenzene, stryene and other cracking products | 15% |
| Isomerization products cumene and alpha-methylstyrene | 36% |
| Beta-methylstyrene | 21% |
| Allyl-benzene | 4% |
| Indan | 1% |

In this comparative example, large losses to cracking products, isomerization products and other compounds which are not intermediate compounds in the formation of indene illustrate an important advantage of the instant process.

Because the effects of different operating conditions on the product purity and yield have not been exaustively investigated the results of the above tests are not intended to represent optimal embodiments of the instant invention that might be achieved.

What is claimed is:

1. A dehydrocyclization process which comprises contacting ortho-ethyltoluene with a catalyst comprising at least one member selected from the group consisting of (a) crystalline copper aluminum borate and (b) zero valent copper on a support comprising at least one member selected from the group consisting of Al$_4$B$_2$O$_9$ and the crystalline copper aluminum borate, the zero valent copper on the support being formed by the reduction of the crystalline copper aluminum borate, and the dehydrocyclization process being conducted under conditions sufficient to effect cyclization forming a dehydrocyclization product comprising indene.

2. The dehydrocyclization process according to claim 1 wherein the crystalline copper aluminum borate comprises Cu$_2$Al$_6$B$_4$O$_{17}$, having the significant X-ray diffraction lines set forth below:

| (d) Angstroms | Strength |
| --- | --- |
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M. |

3. The dehydrocyclization process according to claim 2 wherein the zero valent copper on the support is formed in situ.

4. The process of claim 1 wherein the dehydrocyclization is carried out under vapor-phase conditions in a reaction zone and the ortho-ethyltoluene comprises from 1 to 95 volume percent of the gaseous composition.

5. The process of claim 4 wherein a gaseous feed to the reaction zone comprises the ortho-ethyltoluene and at least one compound selected from the group consisting of hydrogen, nitrogen, steam, alkyls of from 1 to 10 carbon atoms, benzene, toluene, and xylene and an effluent is withdrawn from the reaction zone.

6. The process of claim 4 wherein an effluent from the reaction zone is transferred to a separation zone in which the effluent is separated into at least (i) a first fraction lean, i.e., not rich, in the dehydrocyclization product indene and (ii) a second fraction rich in the dehydrocyclization product indene.

7. The process of claim 6 wherein the first fraction is further contacted under vapor-phase conditions with a catalyst consisting essentially of at least one member selected from the group consisting of (a) crystalline copper aluminum borate and (b) zero valent copper on a support formed by the reduction of the crystalline copper aluminum borate.

8. The dehydrocyclization process according to claim 7 wherein the crystalline copper aluminum borate comprises $Cu_2Al_6B_4O_{17}$, having the significant X-ray diffraction liens set forth below:

| (d) Angstroms | Strength |
| --- | --- |
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M. |

9. The dehydrocyclization process according to claim 7 wherein the zero valent copper on the support is formed in situ.

10. The process of claim 6 wherein the first fraction is admixed with the gaseous composition in the reaction zone.

* * * * *

UNITED STATES PATENT AND TRADEMARK OFFICE
CERTIFICATE OF CORRECTION

PATENT NO. : 5,157,182
DATED : Oct. 20, 1992
INVENTOR(S) : McMahon, Patrick E.; Satek, Larry C.

It is certified that error appears in the above-indentified patent and that said Letters Patent is hereby corrected as shown below:

| Col. | Line | |
|------|------|---|
| 1 | 23 | "catalyst consisting of (a)..." should read --catalyst consisting of at least one member selected from the group consisting of (a)...--. |
| 20 | 13 | "diffraction liens" should read --diffraction lines--. |

Signed and Sealed this

Twenty-third Day of August, 1994

Attest:

BRUCE LEHMAN

Attesting Officer

Commissioner of Patents and Trademarks